United States Patent
Roy et al.

(10) Patent No.: US 8,491,626 B2
(45) Date of Patent: Jul. 23, 2013

(54) APPARATUS FOR PERFORMING AN ELECTROSURGICAL PROCEDURE

(75) Inventors: Jeffrey M. Roy, Boulder, CO (US); James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 513 days.

(21) Appl. No.: 12/792,262

(22) Filed: Jun. 2, 2010

(65) Prior Publication Data

US 2011/0301602 A1   Dec. 8, 2011

(51) Int. Cl.
*A61B 17/00* (2006.01)
*A61B 18/14* (2006.01)

(52) U.S. Cl.
USPC .................................. 606/205; 606/51

(58) Field of Classification Search
USPC ...................... 606/51, 52, 205–207
See application file for complete search history.

(56) References Cited

U.S. PATENT DOCUMENTS

| 3,720,896 A | 3/1973 | Beirlein |
| D263,020 S | 2/1982 | Rau, III |
| D295,893 S | 5/1988 | Sharkany et al. |
| D295,894 S | 5/1988 | Sharkany et al. |
| 4,846,171 A | 7/1989 | Kauphusman et al. |
| 5,250,056 A | 10/1993 | Hasson |
| D348,930 S | 7/1994 | Olson |
| 5,454,378 A | 10/1995 | Palmer et al. |
| 5,472,443 A | 12/1995 | Cordis et al. |
| 5,611,798 A | 3/1997 | Eggers |
| D384,413 S | 9/1997 | Zlock et al. |
| 5,954,731 A | 9/1999 | Yoon |
| 5,993,466 A | 11/1999 | Yoon |
| 5,993,467 A | 11/1999 | Yoon |
| D424,694 S | 5/2000 | Tetzlaff et al. |
| D425,201 S | 5/2000 | Tetzlaff et al. |
| 6,096,037 A * | 8/2000 | Mulier et al. .................. 606/49 |
| 6,190,386 B1 | 2/2001 | Rydell |

(Continued)

FOREIGN PATENT DOCUMENTS

| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley (57) ABSTRACT

An endoscopic forceps is provided and includes a housing having a shaft that extends therefrom. An end effector assembly is operatively connected to a distal end of the shaft and includes a pair of first and second jaw members that are pivotably coupled to one another and movable relative to one another. The first and second jaw members are disposed in a first configuration, wherein the first and second jaw members are disposed in spaced relation relative to one another, to a second configuration, wherein the first and second jaw members cooperate to grasp tissue therebetween. A magnetic actuation mechanism is operably coupled to one or both of the first and second jaw members and configured to generate opposing magnetic fields on each of the first jaw and second jaw members to actuate the first and second jaw members between the first and second configurations.

13 Claims, 4 Drawing Sheets

U.S. PATENT DOCUMENTS

| | | | |
|---|---|---|---|
| D449,886 S | 10/2001 | Tetzlaff et al. | |
| D457,958 S | 5/2002 | Dycus et al. | |
| D457,959 S | 5/2002 | Tetzlaff et al. | |
| 6,398,779 B1 | 6/2002 | Buysse et al. | |
| 6,562,037 B2* | 5/2003 | Paton et al. | 606/51 |
| 6,676,660 B2 | 1/2004 | Wampler et al. | |
| 6,699,240 B2* | 3/2004 | Francischelli | 606/32 |
| D493,888 S | 8/2004 | Reschke | |
| 6,786,905 B2 | 9/2004 | Swanson et al. | |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,303,557 B2 | 12/2007 | Wham et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,686,827 B2 | 3/2010 | Hushka | |
| 7,766,910 B2 | 8/2010 | Hixson | |
| 7,887,536 B2 | 2/2011 | Johnson et al. | |
| 7,918,848 B2 | 4/2011 | Lau | |
| 7,951,150 B2 | 5/2011 | Johnson et al. | |
| 8,016,827 B2 | 9/2011 | Chojin | |
| 8,112,871 B2 | 2/2012 | Brandt et al. | |
| 8,114,122 B2 | 2/2012 | Nau, Jr. | |
| 8,133,254 B2 | 3/2012 | Dumbauld et al. | |
| 8,142,473 B2 | 3/2012 | Cunningham | |
| 8,162,965 B2 | 4/2012 | Reschke et al. | |
| 8,187,273 B2 | 5/2012 | Kerr et al. | |
| 8,197,479 B2 | 6/2012 | Olson et al. | |
| 8,221,415 B2* | 7/2012 | Francischelli | 606/49 |
| 8,226,650 B2 | 7/2012 | Kerr | |
| 8,251,994 B2 | 8/2012 | McKenna et al. | |
| 8,266,783 B2 | 9/2012 | Brandt et al. | |
| 8,277,446 B2 | 10/2012 | Heard | |
| 8,277,447 B2 | 10/2012 | Garrison et al. | |
| 8,282,634 B2 | 10/2012 | Cunningham et al. | |
| 8,287,536 B2 | 10/2012 | Mueller et al. | |
| 8,292,886 B2 | 10/2012 | Kerr et al. | |
| 8,323,310 B2 | 12/2012 | Kingsley | |
| 8,343,150 B2 | 1/2013 | Artale | |
| 8,343,151 B2 | 1/2013 | Siebrecht et al. | |
| 8,357,159 B2 | 1/2013 | Romero | |
| 2001/0041911 A1* | 11/2001 | Dittrich et al. | 606/205 |
| 2004/0073238 A1 | 4/2004 | Makower | |
| 2005/0059858 A1 | 3/2005 | Frith et al. | |
| 2005/0101951 A1 | 5/2005 | Wham et al. | |
| 2006/0089670 A1 | 4/2006 | Hushka | |
| 2006/0217697 A1 | 9/2006 | Lau et al. | |
| 2007/0016187 A1 | 1/2007 | Weinberg et al. | |
| 2007/0078456 A1 | 4/2007 | Dumbauld et al. | |
| 2007/0106297 A1 | 5/2007 | Dumbauld et al. | |
| 2007/0173814 A1 | 7/2007 | Hixson et al. | |
| 2007/0260242 A1 | 11/2007 | Dycus et al. | |
| 2009/0261804 A1 | 10/2009 | McKenna et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 20121161 | 4/2002 |
| DE | 10045375 | 10/2002 |
| DE | 20 2007 009317 | 10/2007 |
| DE | 19738457 | 1/2009 |
| EP | 0517243 | 9/1997 |
| EP | 1159926 | 12/2001 |
| EP | 1177771 A1 | 2/2002 |
| EP | 1777771 | 2/2002 |
| EP | 1330991 | 7/2003 |
| EP | 1842500 | 10/2007 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO99/40857 | 8/1999 |
| WO | WO 00/36986 | 6/2000 |
| WO | WO 01/54604 | 8/2001 |
| WO | WO 2005/110264 | 11/2005 |
| WO | WO2008045348 A2 | 4/2008 |
| WO | WO 2009/039510 | 3/2009 |
| WO | WO 2009039179 | 3/2009 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With The LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques", OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4. dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.

Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report EP11168419.7 dated Aug. 8, 2011.
International Search Report EP11168419.7 dated Oct. 11, 2011.
International Search Report EP11168455.1 dated Sep. 26, 2011.
European Search Report for European Application No. 12169753.6 dated Sep. 14, 2012.
European Search Report for European Application No. 11168458.5 dated Jul. 21, 2011.
U.S. Appl. No. 12/246,553, filed Oct. 7, 2008, Roy.
U.S. Appl. No. 12/248,115, filed Oct. 9, 2008, Cunningham et al.
U.S. Appl. No. 12/249,263, filed Oct. 10, 2008, Ward et al.
U.S. Appl. No. 12/254,123, filed Oct. 20, 2008, Hinton.
U.S. Appl. No. 12/336,970, filed Dec. 17, 2008, Sremcich et al.
U.S. Appl. No. 12/353,466, filed Jan. 14, 2009, Twomey et al.
U.S. Appl. No. 12/353,470, filed Jan. 14, 2009, Cunningham.
U.S. Appl. No. 12/410,195, filed Mar. 24, 2009, Nau, Jr. et al.
U.S. Appl. No. 12/434,382, filed May 1, 2009, Rachlin et al.
U.S. Appl. No. 12/508,052, filed Jul. 23, 2009, Moses et al.
U.S. Appl. No. 12/535,869, filed Aug. 5, 2009, Reschke.
U.S. Appl. No. 12/543,831, filed Aug. 19, 2009, Reschke.
U.S. Appl. No. 12/548,534, filed Aug. 27, 2009, Gerhardt et al.
U.S. Appl. No. 12/548,566, filed Aug. 27, 2009, Kappus et al.
U.S. Appl. No. 12/551,944, filed Sep. 1, 2009, Dycus.
U.S. Appl. No. 12/556,407, filed Sep. 9, 2009, Brandt et al.
U.S. Appl. No. 12/556,427, filed Sep. 9, 2009, Mueller.
U.S. Appl. No. 12/556,796, filed Sep. 10, 2009, Harper et al.
U.S. Appl. No. 12/565,281, filed Sep. 23, 2009, Dickhans.
U.S. Appl. No. 12/569,395, filed Sep. 29, 2009, Lee et al.
U.S. Appl. No. 12/574,292, filed Oct. 6, 2009, Kerr et al.
U.S. Appl. No. 12/607,191, filed Oct. 28, 2009, Nau, Jr. et al.
U.S. Appl. No. 12/619,100, filed Nov. 16, 2009, Harper et al.
U.S. Appl. No. 12/690,726, filed Jan. 20, 2010, Johnson et al.
U.S. Appl. No. 12/692,414, filed Jan. 22, 2010, Mueller.
U.S. Appl. No. 12/692,810, filed Jan. 25, 2010, Baily.
U.S. Appl. No. 12/696,592, filed Jan. 29, 2010, Harper et al.
U.S. Appl. No. 12/696,857, filed Jan. 29, 2010, Chojin.
U.S. Appl. No. 12/700,856, filed Feb. 5, 2010, Krapohl.
U.S. Appl. No. 12/719,407, filed Mar. 8, 2010, Reschke.
U.S. Appl. No. 12/728,994, filed Mar. 22, 2010, Chojin et al.
U.S. Appl. No. 12/748,028, filed Mar. 26, 2010, Olson.

\* cited by examiner

APPARATUS FOR PERFORMING AN ELECTROSURGICAL PROCEDURE

BACKGROUND

1. Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

SUMMARY

The present disclosure provides an endoscopic forceps. The endoscopic forceps includes a housing having a shaft that extends therefrom and defines a longitudinal axis therethrough. The first and second jaw members are disposed in a first configuration, wherein the first and second jaw members are disposed in spaced relation relative to one another, to a second configuration, wherein the first and second jaw members cooperate to grasp tissue therebetween. A magnetic actuation mechanism is operably coupled to one or both of the first and second jaw members and configured to generate opposing magnetic fields on each of the first jaw and second jaw members to actuate the first and second jaw members between the first and second configurations.

The present disclosure provides an endoscopic forceps. The endoscopic forceps includes a housing having a shaft that extends therefrom and defines a longitudinal axis therethrough. An end effector assembly is operatively connected to a distal end of the shaft and includes a pair of first and second jaw members. The first and second jaw members are pivotably coupled to one another and movable relative to one another from an open position, wherein the first and second jaw members are disposed in spaced relation relative to one another, to a clamping position, wherein the first and second jaw members cooperate to grasp tissue therebetween. A magnetic actuation mechanism operably couples to each of the first and second jaw members and is configured to generate a magnetic field at each of the first jaw and second jaw members. The magnetic actuation mechanism includes two or more magnets that operably couple to a respective first and second jaw member. When the magnetic field at each of the first and second jaw members is the same polarity, the first and second jaw members are caused to move to the open position and when the magnetic field at the first and second jaw members is a different polarity, the first and second jaw members are cause to move to the clamping position.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
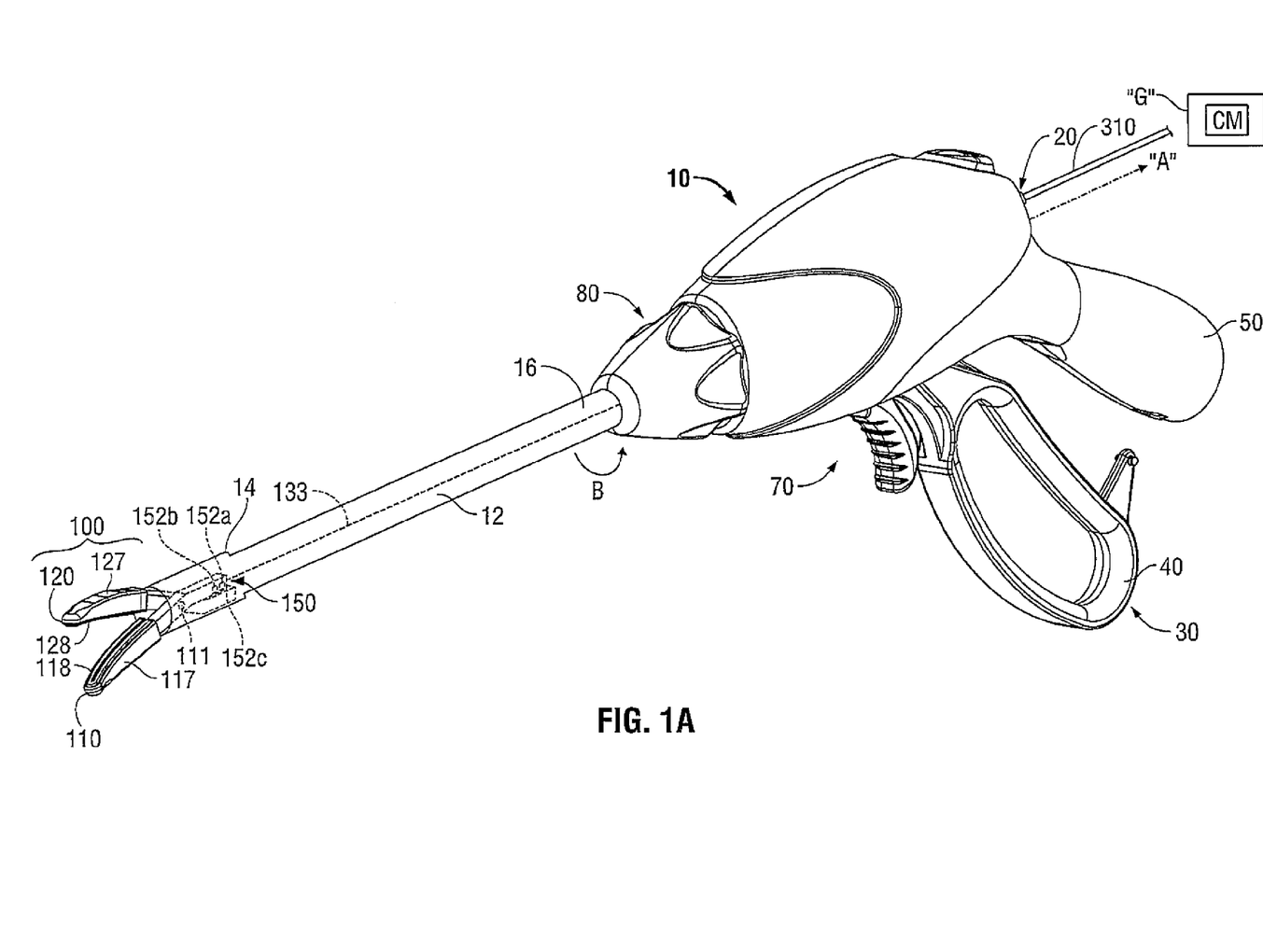
FIG. 1A is a side, perspective view of an endoscopic bipolar forceps showing an end effector assembly including jaw members according to an embodiment of the present disclosure.
Figure 1B:
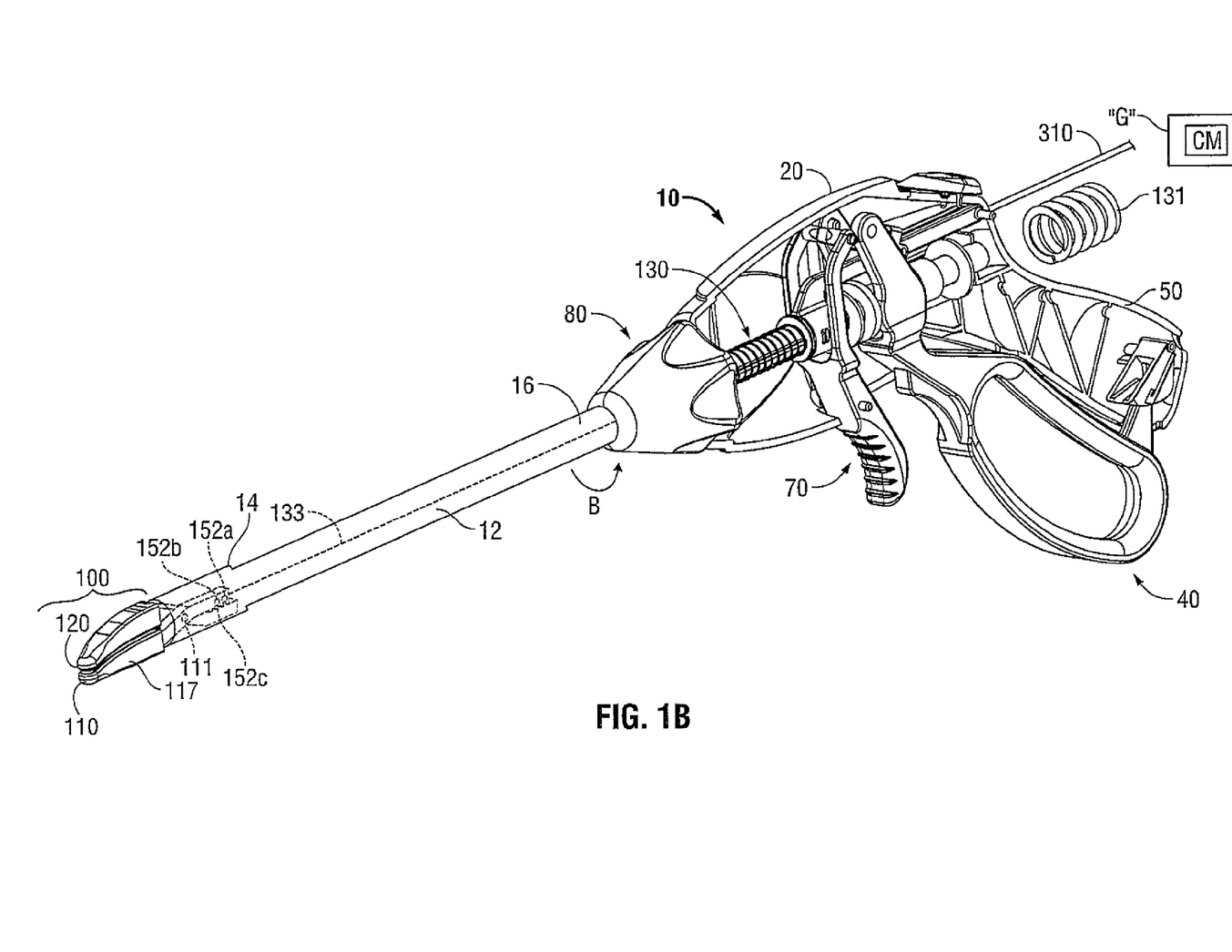
FIG. 1B is a side, perspective view of the endoscopic bipolar forceps depicted in FIG. 1A illustrating internal components associated with a handle assembly associated with the endoscopic bipolar forceps.

With reference to FIGS. 1A and 1B, an illustrative embodiment of an electrosurgical apparatus, e.g., a bipolar forceps 10 (forceps 10) is shown. Forceps 10 is operatively and selectively coupled to an electrosurgical generator ("G") for performing an electrosurgical procedure. As noted above, an electrosurgical procedure may include sealing, cutting, cauterizing, coagulating, desiccating, and fulgurating tissue all of which may employ RF energy. The electrosurgical generator "G" may be configured for monopolar and/or bipolar modes of operation and may include or be in operative communication with a system that may include one or more processors in operative communication with one or more control modules "CM" that are executable on the processor. The control module CM may be configured to instruct one or more modules to transmit electrosurgical energy, which may be in the form of a wave or signal/pulse, via one or more cables (e.g., an electrosurgical cable 310) to the forceps 10. In certain embodiments, the control module "CM" is configured control current flow through to a magnetic actuation mechanism 250 (FIGS. 3A and 3B) to adjust the polarity of an electromagnetic field that is generated by magnetic actuation mechanism 250, described in greater detail below.

Forceps 10 is shown configured for use with various electrosurgical procedures and generally includes a housing 20, electrosurgical cable 310 that connects the forceps 10 to the electrosurgical generator "G," a rotating assembly 80 and a trigger assembly 70. For a more detailed description of the rotating assembly 80, trigger assembly 70, and electrosurgical cable 310 (including line-feed configurations and/or connections), reference is made to commonly-owned U.S. patent application Ser. No. 11/595,194 filed on Nov. 9, 2006, now U.S. Patent Publication No. 2007/0173814.

With continued reference to FIGS. 1A and 1B, forceps 10 includes a shaft 12 that has a distal end 14 configured to mechanically engage an end effector assembly 100 operably associated with the forceps 10 and a proximal end 16 that mechanically engages the housing 20. Shaft 12 may have any suitable flexibility. For example, in an endoluminal embodiment, shaft 12 may possess the flexibility of a flexible catheter that is utilized to traverse natural orifices. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and movable handle 40. In one particular embodiment, fixed handle 50 is integrally associated with housing 20 and handle 40 is movable relative to fixed handle 50 for effecting movement of one or more components, e.g., a drive wire 133, operably associated with a drive assembly 130 (FIG. 1B) via one or more suitable mechanical interfaces, e.g., a linkage interface, gear interface, or combination thereof.

Drive assembly 130 is in operative communication with handle assembly 30 (see FIGS. 1A and 1B) for imparting movement of one or both of a pair of jaw members 110, 120 of end effector assembly 100, described in greater detail below. Conventional drive assemblies typically utilize one or more types of springs, e.g., a compression spring, to facilitate closing the jaw members 110 and 120. For illustrative purposes, a compression spring 131 (see FIG. 1B) is shown separated from the housing 20. In accordance with the present disclosure, the combination of the drive assembly 130 including a drive wire 133 that operably couples to magnetic actuation mechanism 150, which, in turn, is operably associated with one or both of the jaw members 110 and 120 and functions to facilitate closing the jaw members 110 and 120 thereby eliminating the need for the compression spring 131.

Figure 2A:
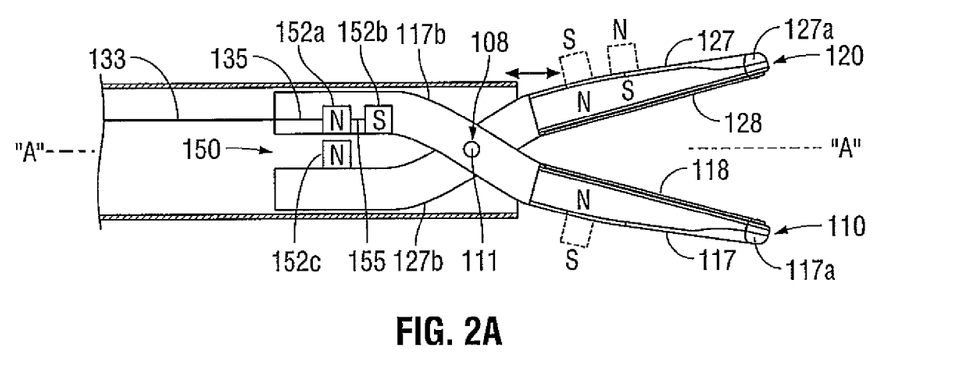
FIGS. 2A and 2B are schematic views of the jaw members depicted in FIGS. 1A and 1B.
Figure 2B:
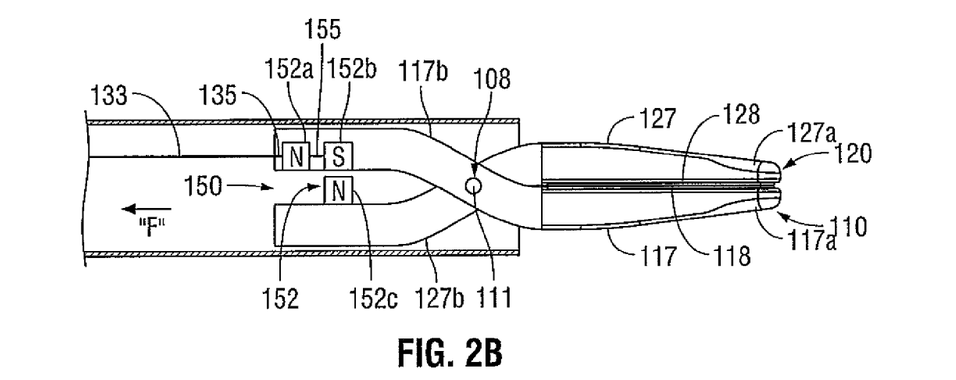

Drive wire 133 is configured such that proximal movement thereof causes jaw member 110 and 120 to move from the open position (FIGS. 1A and 2A) to the closed or clamping position (FIGS. 1B and 2B). To this end, drive wire 133 is in operative communication with magnetic actuation mechanism 150. More particularly, a distal end 135 of the drive wire 133 operably couples, by any suitable coupling methods, to magnets 152 that are operably coupled to jaw members 110 and 120. In the illustrated embodiment, distal end 135 operably couples to a proximal end of one of the magnets 152 via one of soldering, brazing, and welding (FIGS. 2A and 2B).

Referring now to FIGS. 2A and 2B, magnetic actuation mechanism 150 is illustrated operably coupled to jaw members 110 and 120 and is configured to generate one or more pairs of magnetic fields at each of the jaw members 110 and 120. More particularly, when a particular pair of magnetic fields at the jaw members 110 and 120 is the same polarity, the jaw members 110 and 120 are caused to move to the open position, and when a particular pair of magnetic fields at the jaw members 110 and 120 is a different polarity, the jaw members 110 and 120 are caused to move to the closed or clamping position. This is described in greater detail below.

To this end, magnetic actuation mechanism 150 includes one or more types of magnets 152. In the embodiment illustrated in FIGS. 2A and 2B, the magnetic actuation mechanism 150 includes three magnets 152a, 152b, and 152c that are operably disposed on the jaw members 110 and 120. Magnets 152a-152c may be any suitable type of magnet, including, but not limited to permanent magnets, electromagnets, etc. In the embodiment illustrated in FIGS. 2A and 2B, each of magnets 152a-152c is a permanent magnet that is capable of creating a magnetic field of suitable proportion. For illustrative purposes, magnets 152a and 152c are shown generating a magnetic field having a northern polarity and magnet 152b is shown generating magnetic field having a southern polarity. The magnetic field generated by each of the magnets 152a and 152c provides a sufficient "repelling" force to adequately open the jaw members 110a and 120, e.g., enough to position tissue between the jaw members 110a and 120. Moreover, the magnetic fields generated by each of the magnets 152b and 152c provides a sufficient "attracting" force to adequately close the jaw members 110 and 120. For example, in one embodiment, a closure force in the range of about 3 kg/cm$^2$ to about 16 kg/cm$^2$ at the jaw members 110 and 120 for sealing tissue is contemplated.

For illustrative purposes, magnets 152a and 152b are shown operably coupled to jaw member 110 and magnet 152c is shown operably coupled to jaw member 120. Each of the magnets 152a-152c is illustrated operably disposed on the respective jaw members 110 and 120 at a location that is proximal a pivot pin 111 that pivotably couples the jaw members 110 and 120 to each (FIGS. 2A and 2B). Alternatively, each of the magnets 152a-152c may be operably disposed on the respective jaw members 110 and 120 at a location that is distal the pivot pin 111, shown in phantom in FIG. 2A. The magnets 152a-152c are positioned/oriented on the proximal end of the respective jaw member such that the magnetic field that is generated by the magnets is concentrated toward the longitudinal axis "A-A." Positioning/orienting the magnets 152a-152c in this manner facilitates moving the jaw members 110 and 120 from the open position to the closed or clamping position or vice versa.

Magnets 152a and 152b are slidably or movably coupled to jaw member 110 via one or more suitable coupling methods. More particularly, a channel/detent configuration couples the magnets 152a and 152b to a proximal end 117b of the jaw member 110. In this instance, a bottom portion of the magnets 152*a* and 152*b* may include a detent (not shown) that operably engages a corresponding channel (not shown) located on the proximal portion 117*b* of jaw member 110. In the embodiment illustrated in FIGS. 2A and 2B, magnets 152*a* and 152*b* translate or slide along or within the channel and relative to the jaw member 110 and magnet 152*c* when the drive wire 133 is move proximally and/or distally. A proximal end of the magnet 152*a* operably couples to distal end 135 of the drive wire 133 (FIG. 2A) via one or more the aforementioned coupling methods, e.g., soldering.

Magnets 152*a* and 152*b* move in unison. That is magnets 152*a* and 152*b* are configured such that movement of the magnet 152*a* in one direction, e.g., a proximal and/or distal direction, causes proportionate movement of the magnet 152*b* in the same direction. To this end, magnets 152*a* and 152*b* operably couple to one another via one or more suitable coupling methods. In the embodiment illustrated in FIGS. 2A and 2B, magnets 152*a* and 152*b* operably couple to one another via a substantially rigid rod 155, cable, cord or the like.

Magnet 152*c* is a stationary magnet. That is, magnet 152*c* is fixedly coupled to a proximal end 127*b* of jaw member 120 via one or more suitable coupling methods, e.g., a heat cure epoxy.

While the magnetic actuation mechanism 150 provides that magnets 152*a* and 152*b* are movable and magnet 152*c* is stationary, it is within the purview of the present disclosure to have magnets 152*a* and 152*b* be stationary and the magnet 152*c* may be movable; this, of course, will depend on the contemplated uses of the manufacturer/user.

Continuing with reference to FIGS. 2A and 2B, end effector assembly 100 is illustrated operably disposed at the distal end 14 of the shaft 12. End effector assembly 100 includes opposing jaw members 110 and 120 that mutually cooperate to grasp, seal and, in some cases, divide large tubular vessels and large vascular tissues.

Jaw members 110, 120 are operatively and pivotably coupled to each other and located adjacent the distal end 14 of shaft 12. Respective electrically conductive seal plates 118 and 128 are operably supported on and secured to respective jaw housings 117 and 127 of respective the jaw members 110 and 120. For the purposes herein, jaw members 110 and 120 include jaw housings 117 and 127 that are configured to support sealing plates 118 and 128, respectively. Each of the sealing plates 118 and 128 is identical to each other. Jaw members 110 and 120 including respective jaw housings 117 and 127, and operative components associated therewith, may be formed from any suitable material, including but not limited to metal, metal alloys, plastic, plastic composites, and so forth. In the embodiment illustrated in FIGS. 2A and 2B, each of the jaw members 110 and 120 including respective housings 117 and 127 is formed from a combination of metal and plastic. To ensure that the magnetic fields generated by or associated with the magnets 152*a*-152*c* are not impaired, diminished or altered in any way, or that the proximal ends 117*b* and 127*b* are negligibly affected by these magnetic fields, the proximal ends 117*b* and 127*b* may be coated with, made from and/or insulated by a non-magnetic material, e.g., copper, aluminum, plastic, water, and/or gas.

Proximal end 127*b* of jaw member 110 is proportioned to maintain magnet 152*c* in a substantially fixed or stationary position when the jaw members 110 and 120 are moving from the open to closed or clamped position or vice versa. To this end, proximal end 127*b* includes a generally elongated shape of suitable proportion. In the embodiment illustrated in FIGS. 2A and 2B, magnet 152*c* is shown operably disposed adjacent a medial portion of the proximal end 127*b*.

Unlike proximal end 127*b* of jaw member 120, and as noted above, proximal end 117*b* includes one of a detent/channel configuration that extends substantially along a length of the proximal end 117*b*. The dimensions of the detent/or channel are such that the magnets 152*a* and 152*b* may translate or slide therein or therealong when the drive wire 133 is moved proximally and/or distally. To facilitate moving the magnets 152*a* and 152*b* along the channel, one or more types of lubricious materials, e.g., bio-compatible grease, may added to one or both of the detent and/or channel.

The jaw members 110 and 120 may be coupled to each other via any suitable coupling methods. In the illustrated embodiment, an opening 108 is defined in and extends through the each of the jaw housing 117 and 127 and is configured to receive a pivot pin 111. Opening 108 is shown engaged with pivot pin 111 and as such is not explicitly visible.

In an assembled configuration pivot pin 111 is positioned within the openings associated with each of the jaw members 110 and 120. Once assembled, the jaw members 110 and 120 may be pivotably supported at the distal end 14 of the shaft 12 by known methods, such as, for example, by the method described in commonly-owned U.S. patent application Ser. No. 11/827,297.

In the assembled configuration the spacing between the proximal end 117*b* and 127*b* is such that the jaw members 110 and 120 are capable of sufficiently opening, i.e., when the magnets 152*a* and 152*c* are substantially aligned (FIG. 2A) and closing, i.e., when the magnets 152*b* and 152*c* are substantially aligned (FIG. 2B).

In use, initially jaw members 110 and 120 are positioned in an open configuration with the magnets 152*a* and 152*c* in substantial alignment with each other (FIGS. 1A and 2A). Tissue is positioned between the jaw members 110 and 120. Movable handle 40 is moved proximally (FIG. 1B), which, in turn, causes the drive wire 133 to move proximally in the direction indicated by directional arrow "F" (FIG. 2B). Proximal movement of the drive wire 133 causes the magnets 152*a* and 152*b* to move proximally, which, in turn, causes the magnets 152*a* and 152*c* to move out of alignment with each other and magnets 152*b* and 152*c* to move into alignment with each other (FIG. 2B). As the magnets 152*ba* and 152*c* move into alignment with each other the jaw members 110 and 120 move toward one another such that tissue is grasped between the jaw members 110 and 120 (FIG. 2B). Subsequently, electrosurgical energy is transmitted to the seal plates 118 and 128 such that an electrosurgical effect, e.g., a tissue seal, is achieved at tissue. Alternatively, the forceps 10 may be used for grasping tissue and, as such, energy is not supplied to the seal plates 118 and 128, nor is there an electrical connection to an energy source.

The magnetic actuation mechanism 150 associated with the jaw members 110 and 120 provides an additional mechanical advantage at the jaws 110 and 120 and reduces the frictional losses that may be associated with a forceps with a flexible shaft when a drive element is translated within the shaft to make the necessary closure force to seal tissue, e.g., the closure force is offloaded and/or diminished by the drive assembly including drive wire 133 and magnetic actuation mechanism 150.

In lieu of a drive wire 133, the magnets 152*a* and 152*b* may be electrically charged. In a neutral position, the jaw members 110 and 120 are biased in an open position. When electrical energy is applied to one or both of the jaw members 110 and 120, the jaw members 110 and 120 are closed with the appropriate pressure. As such, no moving parts, e.g., a drive wire 133, are translated through the shaft 12.

Figure 3A:
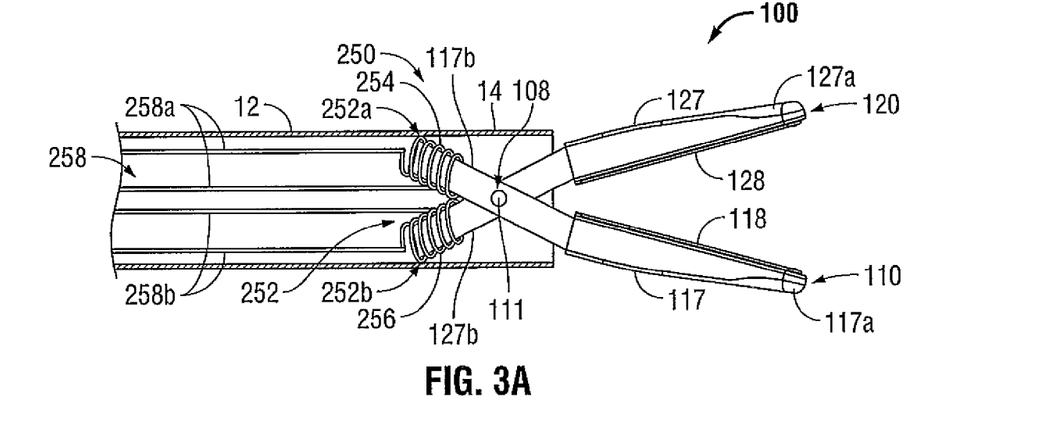
FIGS. 3A and 3B are schematic views of an alternate embodiment of the jaw members depicted in FIGS. 2A and 2B.
Figure 3B:
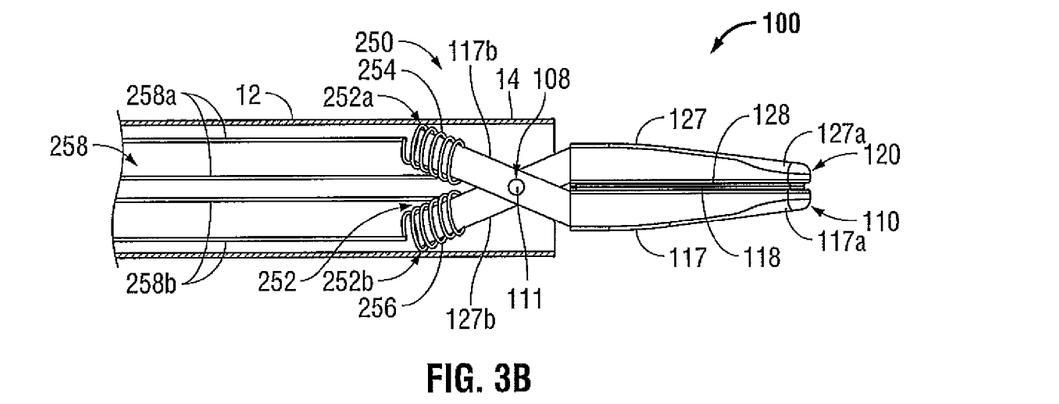

With reference now to FIGS. 3A and 3B, an alternate embodiment of a magnetic actuation mechanism is shown designated 250. Magnetic actuation mechanism 250 is similar to that of magnetic actuation mechanism 150. A distinguishing feature of magnetic actuation mechanism 250 when compared to magnetic actuation mechanism 150 is that magnetic actuation mechanism includes one or more electromagnets 252. More particularly, and in the embodiment illustrated in FIGS. 3A and 3B, two electromagnets 252a and 252b are operably associated with or operably disposed on a respective jaw member 110 and 120. It should be noted that electromagnets 252a and 252b are substantially identical to each other. In view thereof, and so as not to obscure the present disclosure with redundant information, the operative components associated with electromagnet 252a are described in further detail, and only those features distinct to electromagnets 252b will be described hereinafter.

In the embodiment illustrated in FIGS. 3A and 3B, electromagnet 252a is operably coupled to a proximal end 117b of jaw member 110. More particularly, electromagnet 252a includes a coil 254 that substantially encircles the proximal end 117b (FIG. 3A). To enhance or increase the magnetic field generated by the electromagnet 252a, one or more types of ferromagnetic materials, e.g., iron, may be operably disposed on the jaw member 110 adjacent the coil 254. More particularly, and in the embodiment illustrated in FIGS. 3A and 3B, proximal end 117b, or portion thereof, is made from a soft iron and coil 254 extends substantially along a length of thereof substantially encircling the iron.

Similarly, electromagnet 252b includes a coil 256 that substantially encircles the proximal end 127b (FIG. 3A). As with electromagnet 252a, to enhance or increase the magnetic field generated by the electromagnet 252b, one or more types of ferromagnetic materials, e.g., soft iron, may be operably disposed on the jaw member 120 adjacent the coil 256.

Current flow through the coil 254 in a first direction provides an electromagnetic field having a corresponding polarity, e.g., northern polarity, and current flow through the coil 254 in a second direction provides an electromagnetic field having a corresponding polarity, e.g., southern polarity. Likewise, current flow through the coil 256 in a first direction provides an electromagnetic field having a corresponding polarity, e.g., northern polarity, and current flow through the coil 256 in a second direction provides an electromagnetic field having a corresponding polarity, e.g., southern polarity.

One or more leads provide an electrical interface from the electromagnets 252a and 252b to the electrosurgical generator "G." More particularly, leads 258a operably couple to coil 254 of electromagnet 252a and leads 258b operably couple to coil 256 of electromagnet 256. Leads 258a and 258b supply current to the electromagnets 252a and 252b based on input signals provided by the control module "CM" that is operably associated with the electrosurgical generator "G."

Control module "CM" utilizes one or more control algorithms to control current flow through each of the electromagnets 252a and 252b and respective coils 254 and 256. Thus, to move the jaw members 110 and 120 to the opened position, the electromagnets 252a and 252b will have the same polarity, e.g., a northern polarity, and repel one another. And, to move the jaw members 110 and 120 to the closed or clamped position, the electromagnets 252a and 252b will have different polarities, e.g., electromagnetic 252a will have a northern polarity and the electromagnet 252b will have a southern polarity, and attract one another.

Control module "CM" is configured to control the closure force at the jaw members 110 and 120. More particularly, the one or more control algorithms is part of a closed loop feedback system that is deigned to monitor and/or control the amount of current that is transmitted to the electromagnets 252a and 252b. Thus, in the instance where a greater closure force is required at the jaw members 110 and 120, control module "CM" signals for more current to one or both of the jaw members 110 and 120. Similarly, in the instance where a lesser closure force is required at the jaw members 110 and 120, control module "CM" signals for less current to one or both of the jaw members 110 and 120. In this instance, it is easier to customize pressure based in tissue type or size.

Operation of the forceps 10 that includes jaw members 110 and 120 configured in a manner illustrated in FIGS. 3A and 3B is substantially similar that as previously described above with respect to FIGS. 2A and 2B. A distinguishing feature of the operation of the forceps 10 with the jaw members depicted in FIGS. 3A and 3B when compared to the operation of the forceps 10 with the jaw members depicted in FIGS. 2A and 2B, is that the polarity of the electromagnetic field that is generated by electromagnets 252a and 252b may change or be adjusted based on control signals provided by the control module "CM."

In use, initially jaw members 110 and 120 are positioned in an open configuration with the magnets 252a and 252c having the same polarity, e.g., southern polarity (FIGS. 1A and 3A). Tissue is positioned between the jaw members 110 and 120. To close the jaw members control module "CM" alters current through one of the electromagnets, e.g., electromagnet 252a, such that the electromagnets 252a and 252b have different polarities, e.g., electromagnet 252a has a northern polarity and electromagnet 252b has a southern polarity. The opposite magnetic fields generated by the magnets 252ba and 252b cause the magnets 252a and 252b to attract each other, which, in turn, causes the jaw members 110 and 120 to move toward one another such that tissue is grasped between the jaw members 110 and 120 (FIG. 3B). Subsequently, electrosurgical energy is transmitted to the seal plates 118 and 128 such that an electrosurgical effect, e.g., tissue seal, is achieved at tissue. Again, as mentioned above, the forceps 10 may be used to grasp tissue depending upon a particular purpose. The magnetic actuation mechanism 250 associated with the jaw members 110 and 120 provides an additional mechanical advantage at the jaw members 110 and 120 and reduces the frictional losses that may be associated with a forceps having a flexible shaft when a drive element is translated within the shaft to make the necessary closure force to seal tissue, e.g., the closure force is offloaded and/or diminished by the magnetic actuation mechanism 250. This may be especially true with an articulating instrument or a catheter-based instrument.

Figure 4:
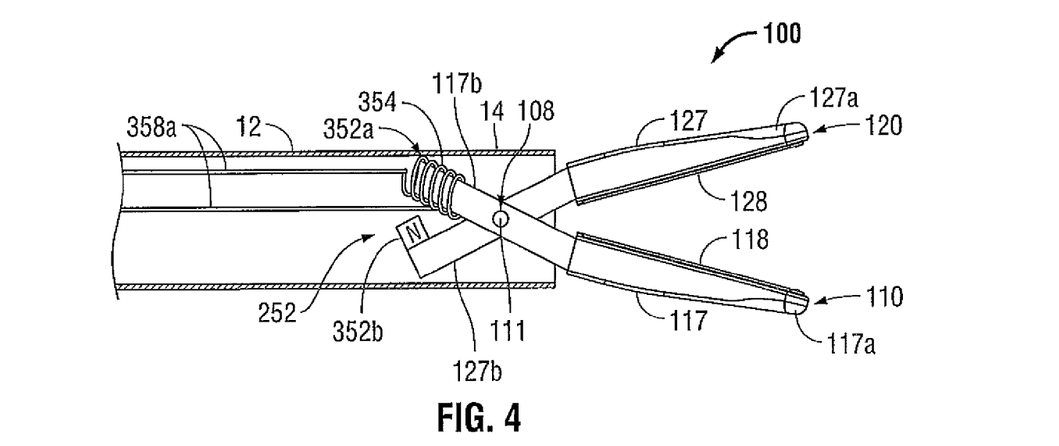
FIG. 4 is a schematic view of an alternate embodiment of the jaw members depicted in FIGS. 3A and 3B.

From the foregoing, and with reference to the various figure drawings, those skilled in the art will appreciate that certain modifications can also be made to the present disclosure without departing from the scope of the same. For example, in one particular embodiment (FIG. 4), forceps 10 may include a magnetic actuation mechanism 350 that includes one or more electromagnets 352a and one or more permanent magnets 352b. In this instance, one of the jaw members, e.g., jaw member 110, may include an electromagnet 352a and the other jaw member, e.g., jaw member 120, may include a permanent magnet 352b. In use, current through the electromagnet 252 is altered accordingly to open and close the jaw members 110 and 120.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
a housing having a shaft that extends therefrom and defines a longitudinal axis therethrough;
an end effector assembly operatively connected to a distal end of the shaft and including a pair of first and second jaw members, the first and second jaw members pivotably coupled to one another and movable relative to one another from a first configuration wherein the jaw members are in spaced relation relative to one another, to a second configuration wherein the jaw members cooperate to grasp tissue therebetween; and
a magnetic actuation mechanism including at least three permanent magnets operably associated with at least one of the first and second jaw members and configured to generate opposing magnetic fields therebetween to actuate the jaw member between the first and second configurations,
wherein at least two of the at least three permanent magnets are operably disposed on one of the first and second jaw members and at least one of the at least three permanent magnets is operably disposed on the other one of the first and second jaw members at a location that is proximal a pivoting member that pivotably couples the first and second jaw members,
wherein the at least two magnets are movable relative to the at least one permanent magnet.

2. An endoscopic forceps according to claim 1, wherein when the opposing magnetic fields at each of the first and second jaw members is the same polarity, the first and second jaw members are caused to move to the first configuration and when the opposing magnetic fields at the first and second jaw members is a different polarity, the first and second jaw members are caused to move to the second configuration.

3. An endoscopic forceps according to claim 1, wherein the at least three magnets are operably disposed on the first and second jaw members at a location that is distal a pivoting member that pivotably couples the first and second jaw members.

4. An endoscopic forceps according to claim 1, wherein the endoscopic forceps further includes a drive assembly operably associated with a movable handle that is operably coupled to the housing, the drive assembly including a drive wire that operably couples to the at least two permanent magnets.

5. An endoscopic forceps according to claim 4, wherein proximal movement of the drive wire causes the magnetic actuation mechanism to move the first and second jaw members from the first configuration to the second configuration.

6. An endoscopic forceps, comprising:
a housing having a shaft that extends therefrom and defines a longitudinal axis therethrough;
an end effector assembly operatively connected to a distal end of the shaft and including a pair of first and second jaw members, the first and second jaw members pivotably coupled to one another and movable relative to one another from a first configuration, wherein the first and second jaw members are disposed in spaced relation relative to one another, to a second configuration, wherein the first and second jaw members cooperate to grasp tissue therebetween; and
a magnetic actuation mechanism operably coupled to each of the first and second jaw members and configured to generate a magnetic field at each of the first jaw and second jaw members, the magnetic actuation mechanism including at least two magnets, wherein each of the at least two magnets operable couple to a respective first and second jaw member,
wherein when the magnetic field at each of the first and second jaw members is the same polarity, the first and second jaw members are caused to move to the first configuration and when the magnetic field at the first and second jaw members is a different polarity, the first and second jaw members are cause to move to the second configuration,
wherein one of the at least two magnets is an electromagnet and the other one of the at least two magnets is a permanent magnet.

7. An endoscopic forceps according to claim 6, wherein the electromagnet is in operative communication with a control module that is in operative communication with an electrosurgical generator configured to supply electrosurgical energy to the endoscopic forceps, the control module configured to control current flow through the electromagnet to adjust the polarity of the electromagnetic field that is generated by the electromagnet.

8. An endoscopic forceps, comprising:
a housing having a shaft that extends therefrom and defines a longitudinal axis therethrough;
an end effector assembly operatively connected to a distal end of the shaft and including a pair of first and second jaw members, the first and second jaw members pivotably coupled to one another and movable relative to one another from a first configuration wherein the jaw members are in spaced relation relative to one another, to a second configuration wherein the jaw members cooperate to grasp tissue therebetween; and
a magnetic actuation mechanism operably associated with at least one of the first and second jaw members and configured to generate opposing magnetic fields therebetween to actuate the jaw member between the first and second configurations,
wherein the magnetic actuation mechanism includes at least two electromagnets configured to provide an electromagnetic field at the first and second jaw members.

9. An endoscopic forceps according to claim 8, wherein at least one of the at least two electromagnets is operably disposed on one of the first and second jaw members and at least one of the at least two electromagnets is operably disposed on the other one of the first and second jaw members.

10. An endoscopic forceps according to claim 8, wherein the at least two electromagnets are operably disposed on the respective first and second jaw members at a location that is proximal a pivoting member that pivotably couples the first and second jaw members.

11. An endoscopic forceps according to claim 8, wherein the at least two electromagnets are in operative communication with a control module that is in operative communication with an electrosurgical generator configured to supply electrosurgical energy to the endoscopic forceps, the control module configured to control current flow through the at least two electromagnets to adjust the polarity of the electromagnetic field that is generated by the at least two electromagnets.

12. An endoscopic forceps according to claim 8, wherein the first and second members include respective proximal ends that are made from a ferromagnetic material.

13. An endoscopic forceps, comprising:
a housing having a shaft that extends therefrom and defines a longitudinal axis therethrough;

an end effector assembly operatively connected to a distal end of the shaft and including a pair of first and second jaw members, the first and second jaw members pivotably coupled to one another and movable relative to one another from a first configuration, wherein the first and second jaw members are disposed in spaced relation relative to one another, to a second configuration, wherein the first and second jaw members cooperate to grasp tissue therebetween; and a magnetic actuation mechanism operably coupled to each of the first and second jaw members and configured to generate a magnetic field at each of the first jaw and second jaw members, the magnetic actuation mechanism including at least two magnets, wherein each of the at least two magnets operable couple to a respective first and second jaw member, wherein when the magnetic field at each of the first and second jaw members is the same polarity, the first and second jaw members are caused to move to the first configuration and when the magnetic field at the first and second jaw members is a different polarity, the first and second jaw members are cause to move to the second configuration, wherein the at least two magnets are operably disposed on the respective first and second jaw members at a location that is proximal a pivoting member that pivotably couples the first and second jaw members.

\* \* \* \* \*